United States Patent [19]

Mattchen

[11] 4,298,074
[45] Nov. 3, 1981

[54] SURGICAL DEVICE USING IMPULSE MOTOR

[75] Inventor: Terry M. Mattchen, Van Nuys, Calif.

[73] Assignee: American Safety Equipment Corporation, Detroit, Mich.

[21] Appl. No.: 712,728

[22] Filed: Aug. 9, 1976

[51] Int. Cl.³ .................. B25D 9/00; A61B 17/18; B23B 5/22

[52] U.S. Cl. .................. 173/129; 128/92 EC; 128/303 R; 173/137; 279/28; 279/75

[58] Field of Search .............. 32/56; 91/276, 290; 128/92 R, 92 A, 92 B, 92 BA, 92 BC, 92 E, 92 EB, 92 EC, 92 ED, 303 R, 305; 173/13, 14, 129, 137; 279/1 Q, 19 R, 19.3, 19.4, 19.6, 19.7, 28, 66, 70, 74, 75

[56] References Cited

U.S. PATENT DOCUMENTS

| | | | |
|---|---|---|---|
| 1,380,118 | 5/1921 | Sparrow | 173/139 X |
| 1,483,085 | 2/1924 | Heidbrink | 128/305 |
| 1,617,969 | 2/1927 | Stevens | 91/276 |
| 1,706,460 | 3/1929 | Norling | 279/75 X |
| 2,172,070 | 9/1939 | Palmgren | 279/74 X |
| 2,267,157 | 12/1941 | Lippincott | 128/92 EB |
| 2,384,434 | 9/1945 | Bettington | 279/28 X |
| 2,518,139 | 8/1950 | Hallowell et al. | 279/75 |
| 2,542,695 | 2/1951 | Neff et al. | 128/303 R X |
| 2,608,413 | 8/1952 | Peck | 279/19 |
| 2,802,340 | 8/1957 | Tallman | 173/129 X |
| 3,232,178 | 2/1966 | Sandvig | 92/171 |
| 3,752,161 | 8/1973 | Bent | 128/303 R X |
| 3,865,200 | 2/1975 | Schmidt | 173/133 X |
| 3,975,032 | 8/1976 | Bent et al. | 279/75 X |
| 4,050,528 | 9/1977 | Foltz et al. | 128/92 B X |

FOREIGN PATENT DOCUMENTS

| | | | |
|---|---|---|---|
| 414676 | 6/1925 | Fed. Rep. of Germany | 128/305 |
| 874855 | 4/1953 | Fed. Rep. of Germany | 279/75 |
| 1283769 | 11/1968 | Fed. Rep. of Germany | 173/118 |
| 137349 | 10/1975 | Norway . | |
| 137350 | 10/1975 | Norway . | |
| 101144 | 3/1941 | Sweden . | |
| 266696 | 5/1950 | Switzerland | 279/75 |
| 316478 | 8/1929 | United Kingdom . | |
| 338696 | 11/1930 | United Kingdom | 91/276 |
| 379444 | 9/1932 | United Kingdom . | |
| 401109 | 11/1933 | United Kingdom | 279/22 |
| 611138 | 10/1948 | United Kingdom . | |
| 1246357 | 9/1971 | United Kingdom . | |
| 1272226 | 4/1972 | United Kingdom . | |
| 1394010 | 5/1975 | United Kingdom . | |
| 128109 | 4/1968 | U.S.S.R. | 128/92 E |

Primary Examiner—Lawrence J. Staab
Attorney, Agent, or Firm—Poms, Smith, Lande & Rose

[57] ABSTRACT

The present surgical tool uses high frequency impulses to replace rotating or oscillating members in cutting through or inserting materials into bone. One embodiment comprises a chisel which uses high frequency impulses to remove bone or other hard material. Because of the high forces developed, a novel holder for the chisel to the tool is disclosed. Another embodiment is a wire driver which uses high frequency impulses to drive wire into bone or other tissue. A novel holder for the wire is disclosed which allows wire to be pulled from the tool so that it can be inserted into the bone but prevents wire from slipping back into the tool during the driving operation. The chisel and the wire are driven by a novel pneumatic impulse motor. The motor includes a piston hammer which is mounted in a chamber, and air ports at either end of the chamber alternately direct air to one side of the piston hammer and to the other side of the piston hammer to drive it along the chamber. A novel valve is provided to control the flow of air between air ports.

4 Claims, 17 Drawing Figures

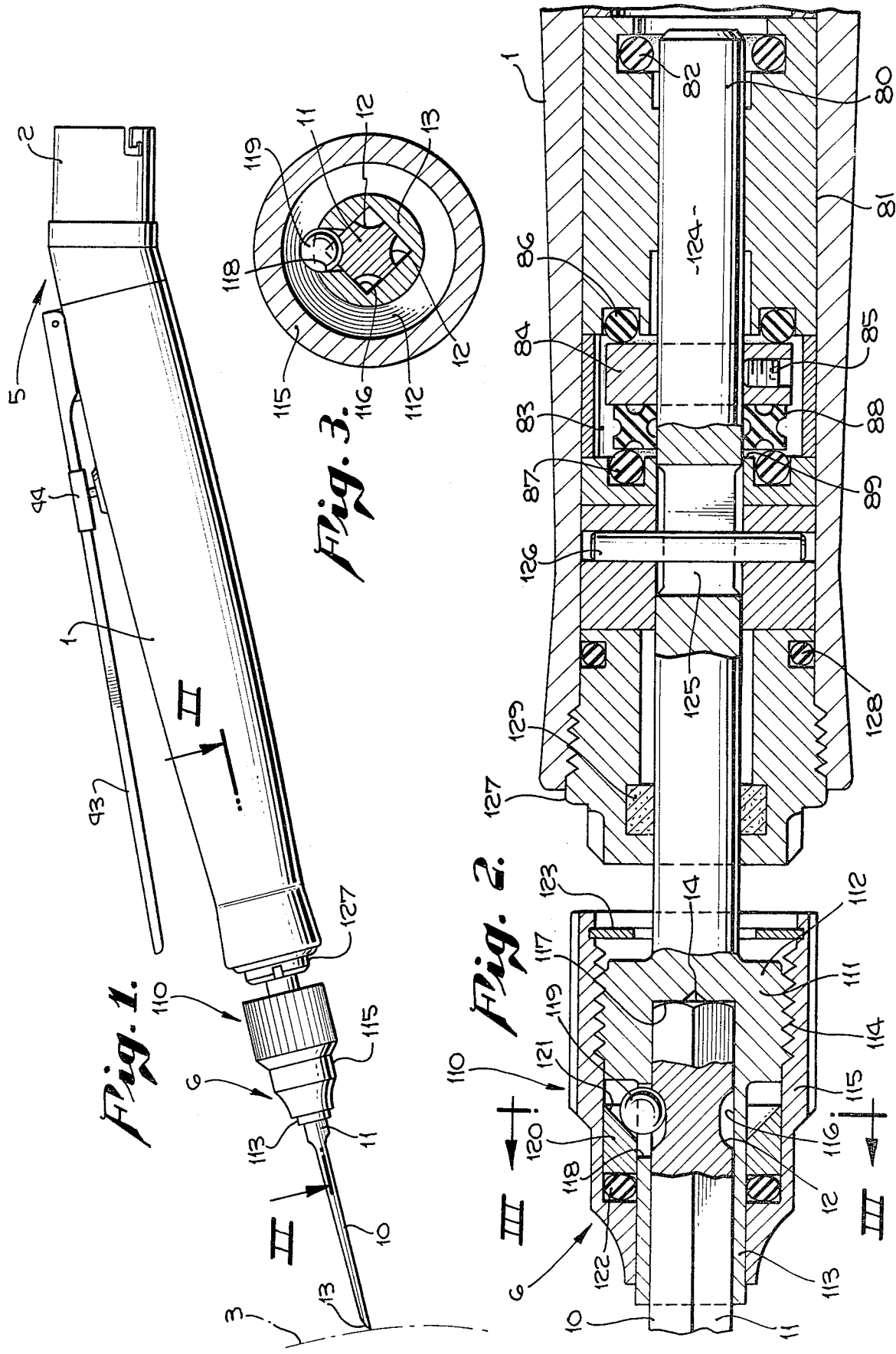

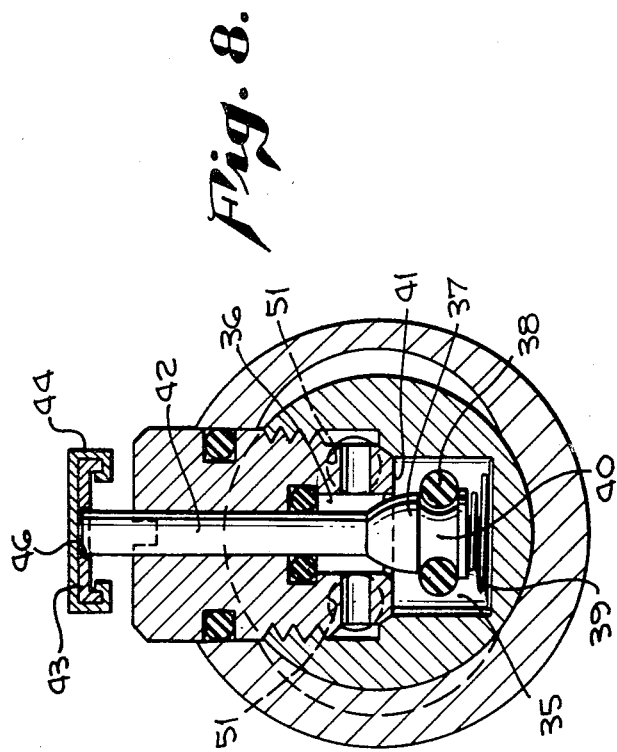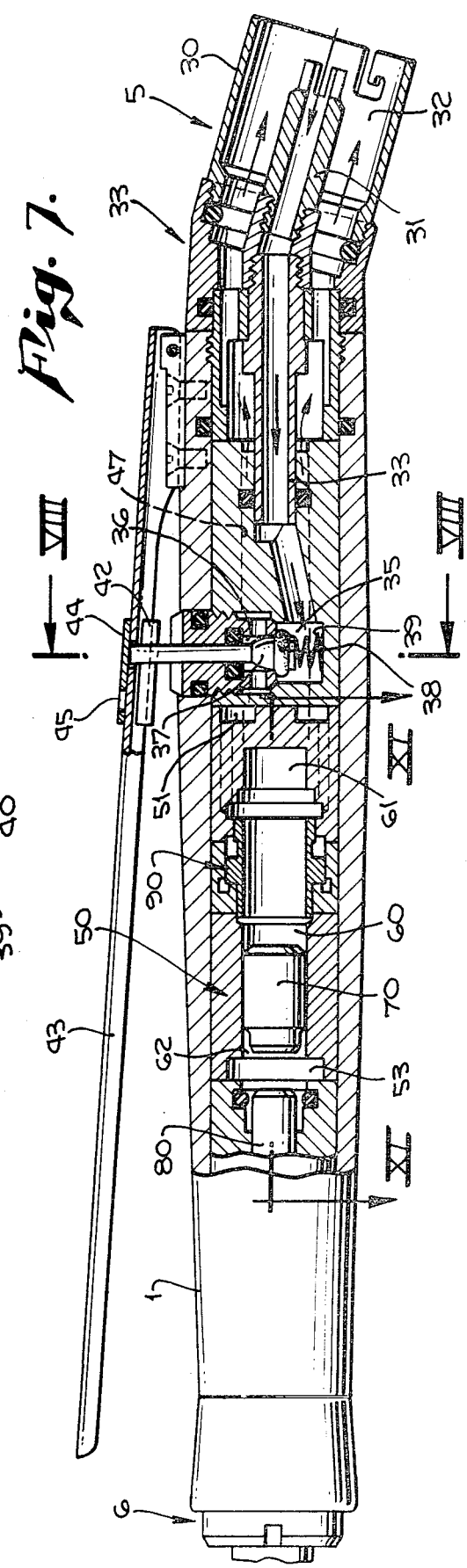

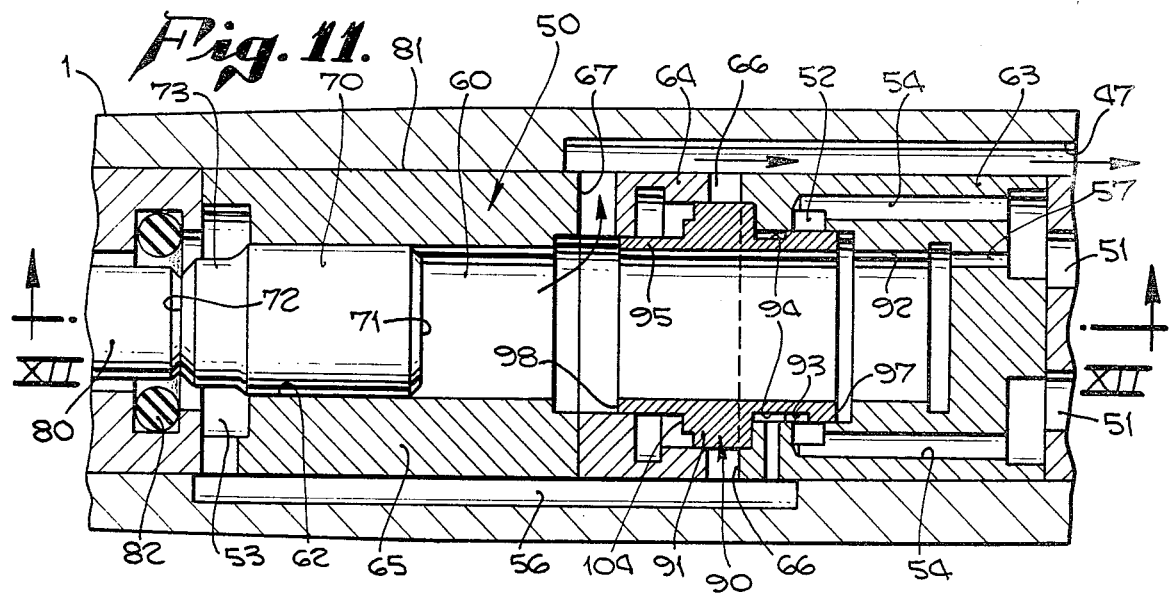
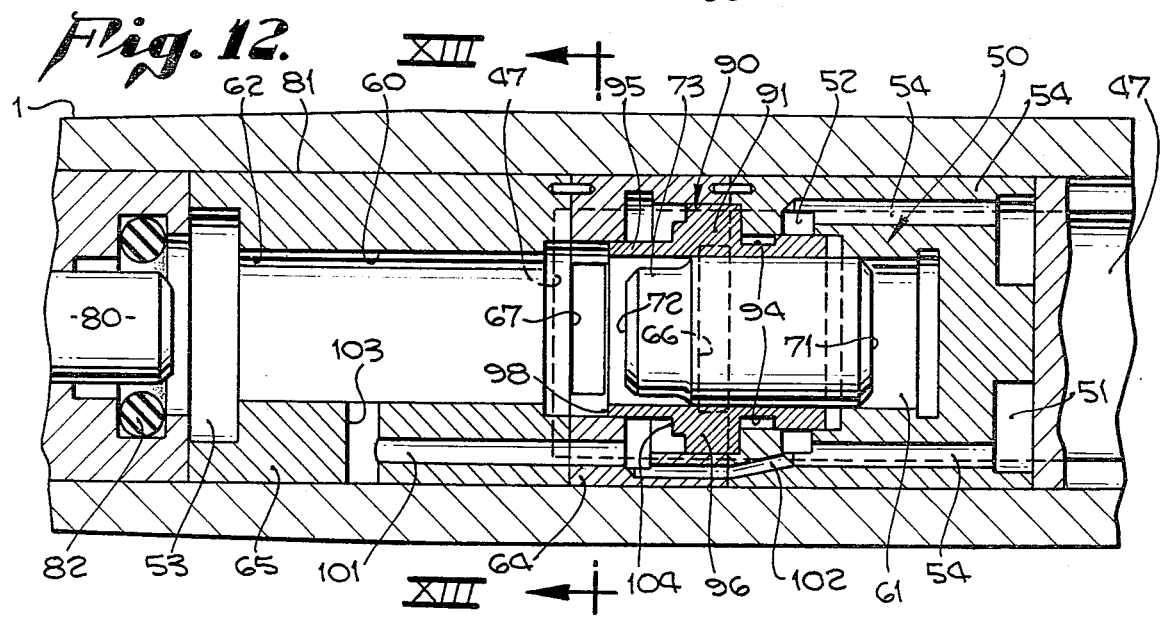
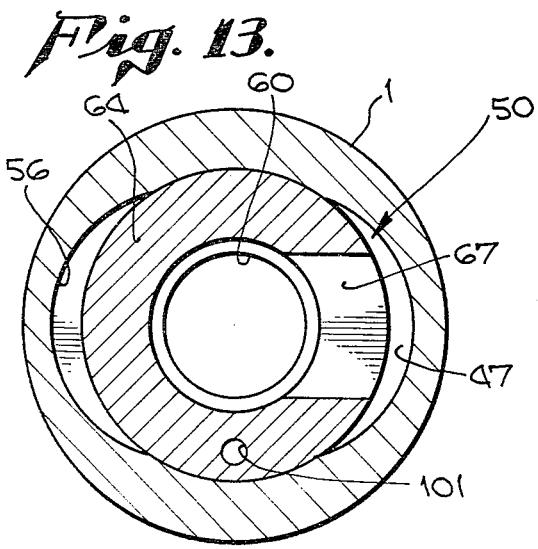
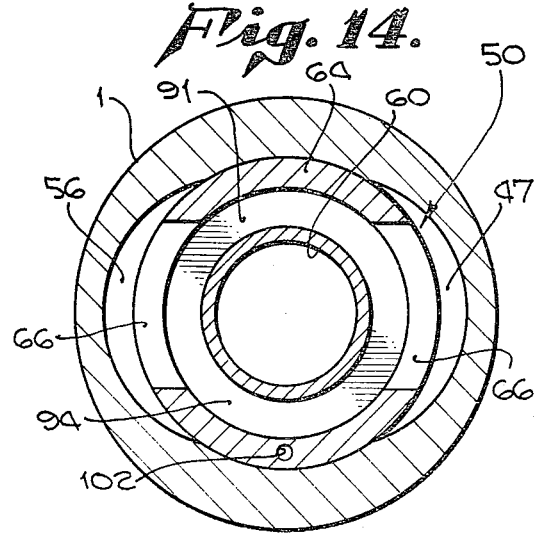

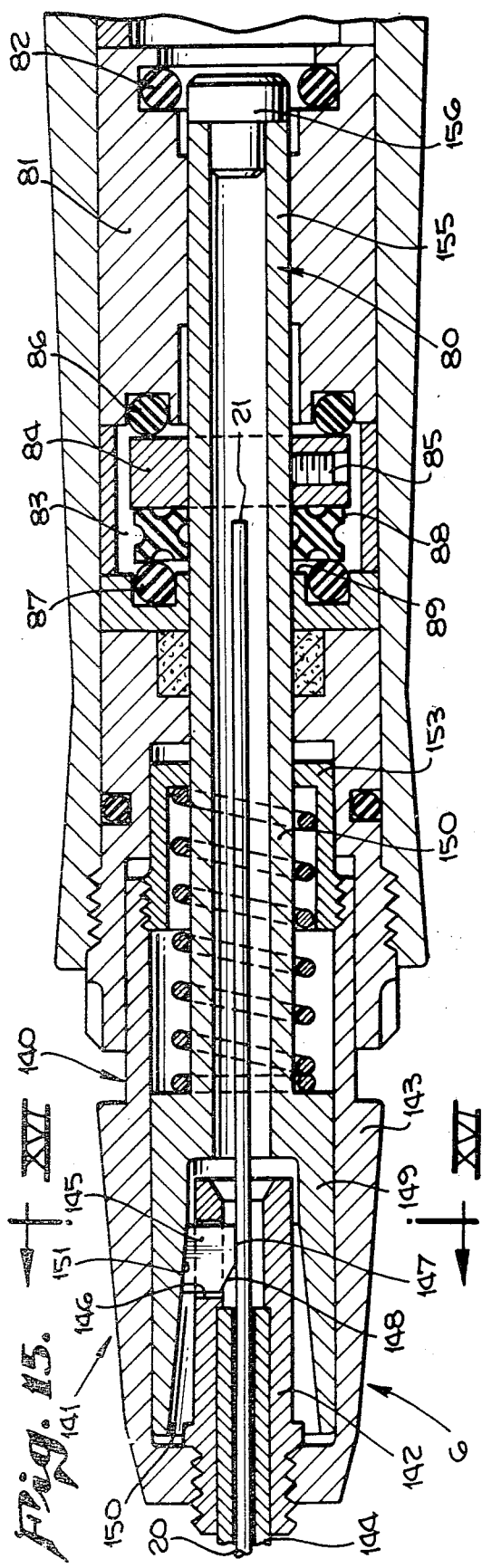
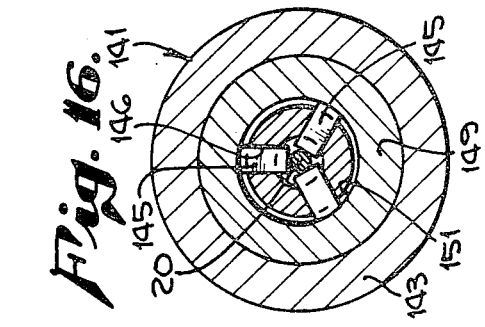
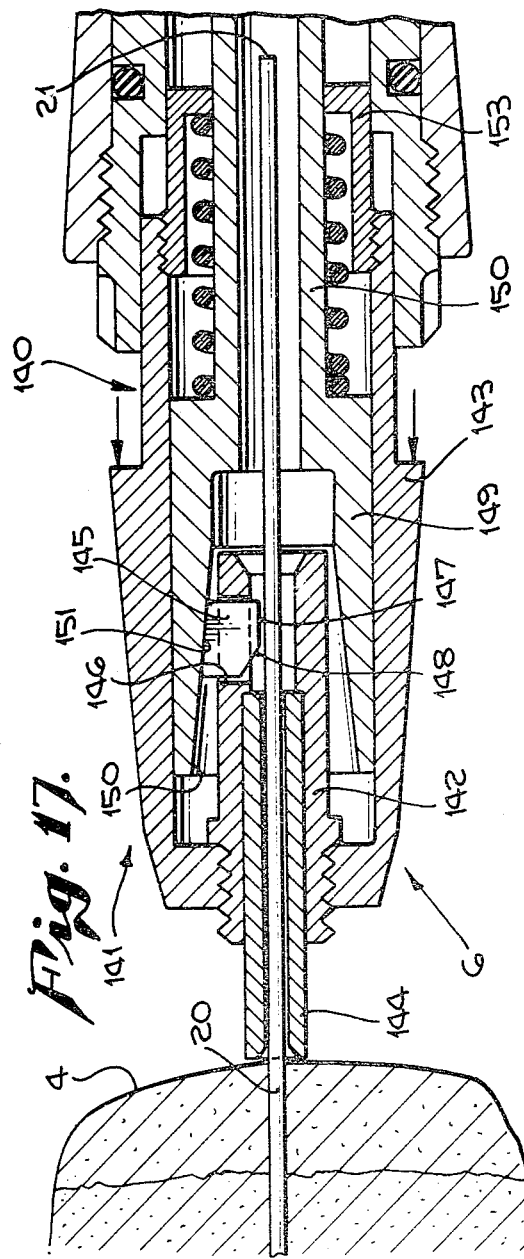

SURGICAL DEVICE USING IMPULSE MOTOR

BACKGROUND OF THE INVENTION

Many surgical tools have been developed in order to accommodate the complex surgical procedures regularly occurring. Most tools use rotary motors and either use the rotation to drive drills, or convert the rotary motion into oscillating or reciprocating motion to drive saws. These tools are highly useful for removing or cutting tissue. In some applications, however, high speed rotation, oscillation or reciprocation creates friction between tissue and the tool, and the resulting heat buildup can create trauma to the tissue.

For example, one surgical procedure requires that wire be inserted into bone. One method mounts the wire in a rotating mandrel, rotates the wire and insert it into the bone. The interaction between the end of the wire and the bone removes tissue. Heat developed at the wire can damage adjacent areas of the bone surrounding the wire insertion. Therefore, the present invention uses high frequency impulses applied to the wire to drive it into the bone. There is little heat buildup and the operation is accomplished quicker than with the rotating method.

Impulses can be obtained by converting rotary motion to reciprocating motion in obtaining impulses from the reciprocating member, but the method has certain drawbacks. First, in a reciprocating system, there is equal force pulling the reciprocating member back to its original position. In the case of a wire driver or chisel, there is no need to have either reciprocate backwards. The backward reciprocation requires a chuck or other holding device which can secure the chisel or wire in the backward direction. Movement of the tool in the backward direction is undesirable in many applications. Another problem is that the power curves for the reciprocating system are improper. Usually the reciprocating systems use a gear arrangement for converting the rotary motion to reciprocating motion. The maximum speed and momentum for the reciprocating member occurs in the middle of the travel rather than at one end of the stroke. A third drawback is the stroke length for the reciprocating system which is usually too long. It is very difficult to compress the stroke length to a short distance. Some systems utilize springs for movement in one direction, but problems are created at high frequencies because springs have natural frequencies. At such frequencies, force may not be applied when needed so that the tool will not operate.

SUMMARY OF THE INVENTION

The following are objects of the invention. One object is to disclose and provide a surgical chisel which operates on high frequency impulses mainly to remove bone and other hard material. Objects associated with the chisel including disclosing and providing means for holding the chisel in the tool so that the impulses will not force the chisel out of the tool; maintaining the chisel in a desired orientation; and preventing the means holding the chisel to the tool from being jammed by the large forces developed during high frequency impacting. Disclosing and providing a wire driver which operates also on high frequency impulses is another object of the invention. With respect to the wire driver, objects include securely holding the wire so that it does not slip during driving; transmitting force to the wire efficiently so that most energy is directed to and through the wire; allowing wire to be easily removed from the tool so that only a short length of wire need project from the tool so that a portion of the short length is driven into the bone, another small length of the wire can be removed from the tool so that it can be driven into the bone. Other objects associated with the wire driver include providing strong securing for the wire in the tool without damaging or shearing the wire. The wire holder must also be designed so that it is not damaged by long term use absorbing forces from the impulse motor.

Other objects include providing a new impulse motor which can provide high frequency impacts to the chisel or wire driver or other tool. With respect to the impulse motor, one object includes having a reliable impulse motor driven by air pressure. Further objects with respect to the impulse motor include having a piston hammer movable down a chamber to impact the output member. Another object is to have the piston hammer driven by air entering the rear of the chamber which is stopped as the piston hammer is contacting the output member, and at the same time, a flow of air must be reversed to enter the front of the chamber to drive the piston hammer back to its original position. Another object is to provide a fast acting reliable valve to quickly switch the flow of air between the front and rear ends of the chamber. Another object of the invention is to have the valve sensitive to pressure differentials in the chamber, the pressure differentials being created in part by movement of the piston hammer. A further object is to cushion the return of the piston hammer to the initial position. Another object of the invention is to return the output member back to a position where it will be contacted by the impact motor. Another object is to disclose and provide a method of impulse driving and wire insertion. Other objects will be evident and some will be discussed in the remainder of this specification.

BRIEF DESCRIPTION OF THE DRAWINGS

FIG. 1 shows the surgical tool of the present invention with the chisel mounted thereon in side elevation.

FIG. 2 is a sectional view taken through plane II—II in FIG. 1 and shows in detail the holding means for holding the chisel to the surgical tool.

FIG. 3 is a sectional view taken through plane III—III in FIG. 2 and shows a ball locking into a detent on the chisel.

FIG. 7 is a side view, partially sectioned showing the impulse motor of the surgical tool and the air control system thereof.

FIG. 8 is a sectional view taken through the plane VIII—VIII of FIG. 7 and shows the valve structure in detail.

FIGS. 9 through 12 are sectional views detailing the operation of the impulse motor. FIG. 9 shows the piston hammer traveling in the driving direction under urging from the primary source of air.

FIG. 10 is a sectional view taken through plane X—X in FIG. 9 and shows the piston hammer in a similar position but different air paths are shown from those shown in FIG. 11.

FIG. 11 is a view similar to that shown in FIG. 9 but shows the piston hammer immediately after having contacted the output member and beginning movement in the return direction.

FIG. 12 is still another detail of the impulse motor in section taken through plane XII—XII in FIG. 11 and shows the hammer almost completing its return to an initial position.

FIG. 13 is a sectional view taken through plane XIII—XIII in FIG. 12 and shows the air conduits.

FIG. 14 also shows air conduits at a different plane in the impulse motor, and is a sectional view taken through plane XIV—XIV in FIG. 10.

FIG. 15 is a sectional view showing the wire driver of the present invention.

FIG. 16 is a sectional view taken through plane XVI—XVI in FIG. 15 and details the wire holder.

FIG. 17 is a sectional view of the wire driver, similar to FIG. 15 but with the wire holder releasing the wire so that it can be pulled from the wire driver.

DETAILED DESCRIPTION OF THE PREFERRED EMBODIMENT

1. The Surgical Tool Generally

Figure 4:
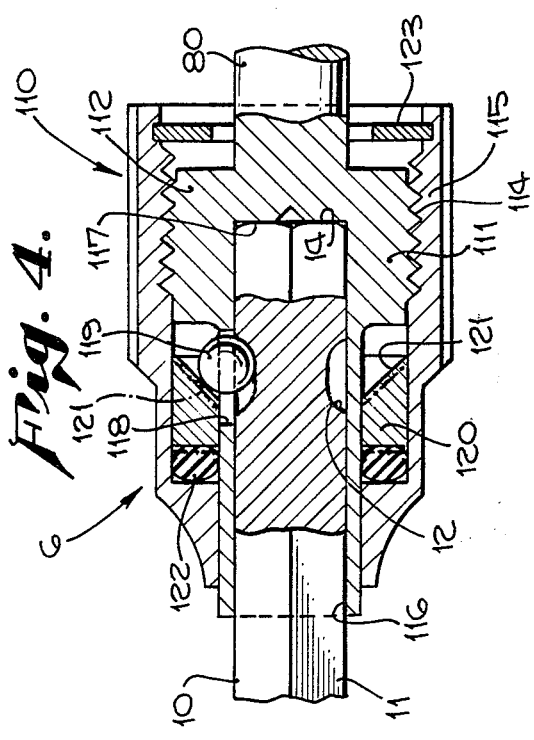
FIG. 4 is a sectional view similar to FIG. 3 but shows the holding means absorbing forces created during impulsing.

The surgical tool of the present invention includes an impulse motor, an output member for removing or trimming or breaking through bone and impulse transmission means for transmitting impulses from the impulse motor to the output member. The impulse motor is mounted in housing 1 which at one end 5 (referred to generally as the rear end) has a swivel fitting 2 which is to be connected to a source of gas. Normally, an inert gas such as nitrogen powers the surgical tool to decrease the chances of igniting volatile chemicals such as ether and to prevent corrosion on internal tool parts. Conventionally, the inert gas is referred to as "air," and that practice will be followed herein.

The housing is formed of a non-corrosive metallic material having characteristics that it can be exposed to high temperatures during sterilizing. The output member shown in FIG. 1 is a chisel which has its main function in removing or trimming hard material such as bone or bone cement 3. The output member may also comprise a wire 20 shown in FIGS. 15 through 17 which mainly is for insertion into hard tissue such as bone 4. The output members are mounted at the output or forward end 6 of the tool.

2. The Impulse Motor Air Supply

As stated above, an important feature of the present invention is its use of impulses to either remove or drive into hard tissue such as bones. As impulse motor to accomplish these results should operate at a high frequency with each impulse having maximum energy. Therefore, the motor of the present invention was developed. Shown generally in FIG. 7 and in more detail in FIGS. 9 through 12, impulse motor 50 comprises a chamber 60 and a piston hammer 70 movable in the chamber from an initial position at the rear end of the chamber to an impacting position impacting impulse transmission means at the forward end of the chamber. Turning again to the preferred exemplary embodiment, the piston hammer in the initial position is near the rear end 61 of chamber 60. The impacting position is shown in FIG. 11 with piston hammer 70 impacting the impulse transmission means 80. The impulse transmission means 80 will be described in more detail hereinafter.

Air supply means for supplying air to the ends of the chamber are provided, and valve means in the chamber direct air to one or the other end of the chamber. Prior to entering the chamber, the air is directed through the valving system. This system is described in more detail in copending application Ser. No. 712,729 filed Aug. 9, 1976 by Terry Mattchen, now abandoned. Briefly, however, an air hose (not shown) carrying high pressure nitrogen ("air") is attached to fitting 30 (FIG. 7) with high pressure air flowing through inlet tube 31 while exhaust air flows around the inlet tube 31 in the exhaust tube 32. The exhaust gas is exhausted into a coaxial air line so that the exhaust takes place away from the surgery. In most instances, a muffler fitting will be mounted near fitting 30 and the air exhausted there. In some applications, it may be necessary to exhaust the air to a remote location through a long coaxial hose.

As shown in FIG. 7, fitting 30 is mounted to a swivel fitting shown generally at 33. The air is directed from inlet 31 through tube 33 and into valve 34. The valve has two chambers, an inlet chamber 35 and an outlet chamber 36. The valve has a poppet which has an O-ring 38 seated in groove 40 in the poppet (FIG. 8). In FIG. 7, O-ring 38 is seated on shoulder 41 which prevents air from passing from inlet chamber 35 into outlet chamber 36. When lever 43 is depressed, valve stem 42 is forced downward facing poppet 36 against the spring 39 so that O-ring 38 moves off shoulder 41. Air can flow from the inlet chamber 35 to outlet chamber 36 to impulse motor 50.

In the preferred embodiment, lever 43 is hinged to housing 1 and extends a substantial length of the housing so that the user can operate the tool in a manner of his choice. A safety slide 44 is slidably mounted along lever 43. Lever 43 has an aperture 46 above the end of the valve stem. The safety slide 44 is slid over aperture 46 so that when the lever 43 is depressed, valve stem 42 is depressed by safety slide 44. Safety slide 44 can be slid so that its aperture 45 is over aperture 46 in the lever 43. In that position, the handle can be depressed without opening the valve. The safety slide is conventional.

3. Details of the Impulse Motor

Air from valve 34 (FIG. 7) enters primary air conduit 51 and then is directed into chamber 60. From primary air conduit 51, air is directed either through rear air port 52, directing air to the rear of the chamber (FIG. 9) or through forward air port 53 directing air to the forward end of the chamber (FIG. 11).

Valve means 90 in the chamber direct air to one end or the other end (61 or 62) of chamber 60. Sensing means on valve means 90 senses the position of piston hammer 70 to change the valve means from directing air to one end of the chamber to directing air to the other end of the chamber. The valve means 90 comprises a valve sleeve 91 and means for mounting the valve sleeve in the chamber for sliding in the chamber. The means for mounting the valve sleeve comprise three members aligned within housing 1, rear member 63, center member 64 and forward member 65. These members also form chamber 60. As seen in comparing FIGS. 9, 10, 11 and 12, members 63–65 have various bores through portions thereof to allow for passage of air. For example, rear port 52 includes a bore 54 through rear member 63 (FIG. 9) to connect it with primary air conduit means 51. The other bores and ports will be described in more detail hereinafter.

The valve means has a drive orientation to direct air from the air supply coming from the primary air conduit to the rear end 61 of the chamber. In the exemplary embodiment, the valve means is shown in its drive direction in FIGS. 9 and 10 where it can be seen that air from the primary air conduit 51 is directed through bore 54 to the rear air port 52. In the exemplary embodiment, there are a series of bores spaced around the rear member 63 to supply sufficient air to the rear air port 52. As air rushes into the rear of the chamber following the path of the arrows, the side of the chamber on the rear of piston hammer 70 becomes pressurized driving piston hammer 70 in a driving direction to the left in FIGS. 9 and 10.

The valve means also has a return orientation, shown primarily in FIGS. 11 and 12 to direct air from the air supply means to the forward end of the chamber to return the piston in a return direction to the initial position. In the exemplary embodiment, valve means 90 is shown in FIGS. 11 and 12 in its return orientation in which it has moved in the chamber to the right from the drive orientation shown in FIGS. 9 and 10.

In the return orientation (FIGS. 7 and 8), air from the primary air conduit 51 is again directed to bores 54 to the rear port 52. However, valve sleeve 91 has a rear air port closing means in the form of flange 92 which substantially covers rear air port 52. The valve sleeve 91 also has a cutout portion 93 (FIG. 11) about part of the flange 92 that covers the rear air port. Cutout portion 93 is connected to notch 94 which extends around valve sleeve 91. When the valve is in the return orientation, notch 94 communicates with air shaft 55 which is connected to channel 56 having forward air port 53 at the forward end thereof. Therefore, when the valve means is in the return orientation, air from the primary air conduit 51 follows the arrows (FIG. 11) and passes through bore 54, cutout 93 and annular notch 94 into shaft 55 where it is directed through channel 56 to the forward port 53.

The piston hammer 70 has a rear face 71 facing the rear end of the chamber and a forward face 72 facing the impact end of the chamber. Face 71 is of a diameter substantially equal to the diameter of the chamber, but face 72 has a diameter approximately equal to the diameter of the impulse transmission means 80. An intermediate face 73 connects the smaller diameter face 72 with the rest of piston hammer 70. Intermediate face 73 is shown curved in the exemplary embodiment, primarily for reasons set forth below, but square walls are also possible. When piston hammer 70 impacts impulse transmission means 80, it is in the location shown in FIG. 11. Air enters forward air port 53, and initially acts on the intermediate face 73 to begin driving the piston hammer in the return direction. Exposure of the forward face 72 allows the air to act on it also. Depending on the inertia resistance of the impulse transmission means 80 and the resistance on the output member relative to the mass of the piston hammer, there will normally be a rebound on the piston hammer so that the air pressure will act across the entire diameter of the front of the piston hammer immediately after impact.

Figure 9:
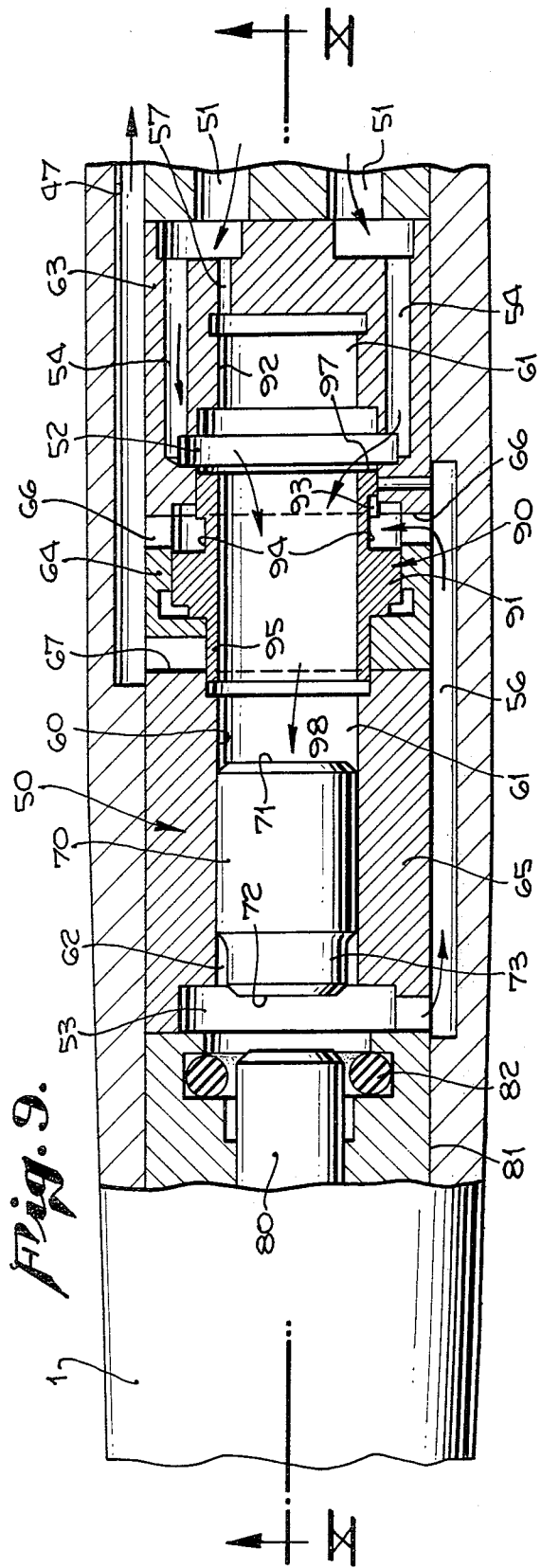
Figure 10:
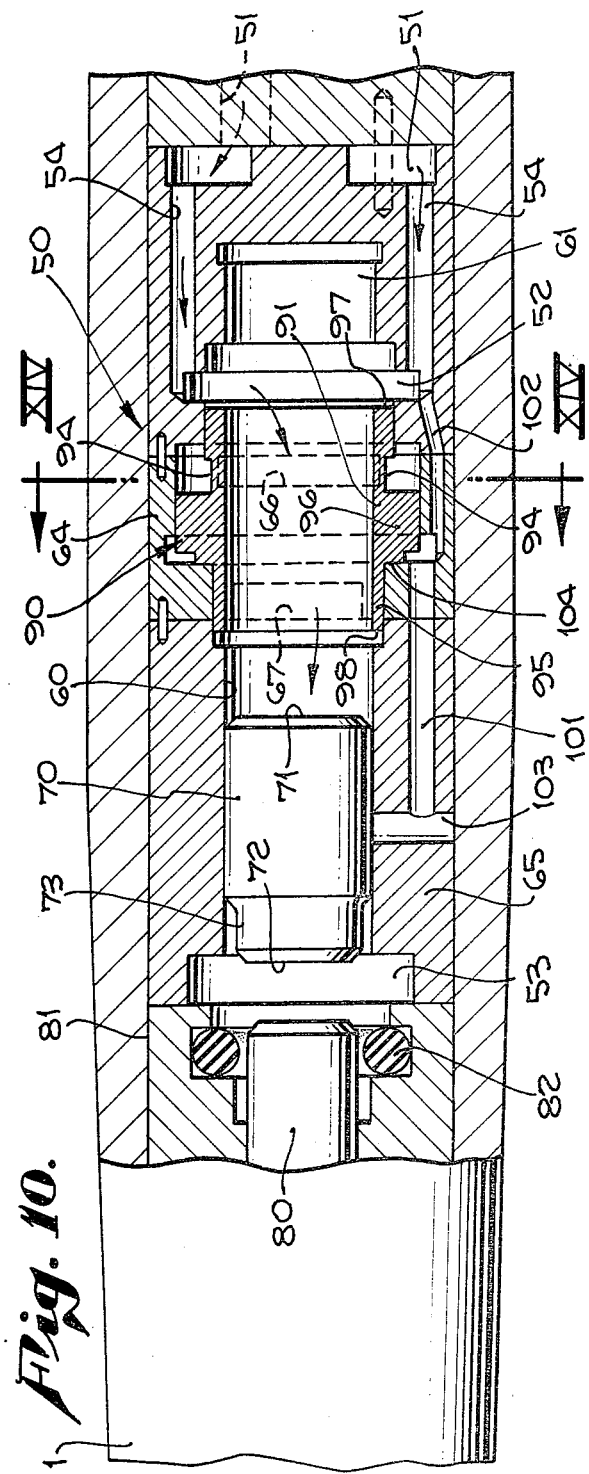

It should also be noted that forward air port 53 is only connected with primary air conduit means 51 when the valve is in the return orientation. As shown in FIG. 9, when the valve means is in the drive orientation, there is no path between bore 54 and channel 56 because the valve sleeve 91 is not located to provide such a path.

After the air has expanded to drive the piston in one direction, it must be exhausted from the chamber in order that it will not cushion movement of the piston hammer in the opposite direction. Therefore, exhaust conduit means comprising rear exhaust port means for allowing air in the rear end of the chamber to escape therefrom and forward exhaust port means for allowing air in the forward end of the chamber to escape therefrom are provided. Turning to the exemplary embodiment, air in the forward end of the chamber is exhausted through the forward air port means 53 into channel 56 where it flows to slot 66 along one edge of center member 64 (FIGS. 9 and 14). Thereafter, it flows through annular notch 94 out the other side of slot 66 to the primary exhaust conduit 47 where it connects with exhaust 32 shown in FIG. 7.

The rear exhaust port comprises a slot 67 at the forward end of center member 64 connecting chamber 60 with exhaust manifold 47 (FIGS. 11 and 13). When the piston hammer 70 is traveling in the return direction indicated by the arrow on piston hammer 70, the air in the chamber follows the path shown by the arrows through slot 67 and into exhaust manifold 47.

The positions of the valve sleeve relative to the exhaust ports should be noted by comparing FIGS. 9 and 11 and by comparing the primary air ports in those figures. When rear air port 52 is open for forcing the piston in the driving direction, the valve sleeve is in a position where slot 66 and annular notch 94 coincide, thereby creating a path for the air out of the forward exhaust port 53 (also the forward air port). When the valve is in the return orientation and the forward air port 53 communicates with the primary air conduit 51 to drive the piston in the return direction, forward flange 95 of the valve sleeve 91 is in a position exposing slot 67 to the chamber so that air can flow out of the chamber, through the slot and into the exhaust manifold 47. When the valve sleeve was in the drive orientation (FIG. 9), forward flange 95 covers slot 67 to prevent air in the chamber from reaching the exhaust manifold 47.

Sensing means on the valve means senses the position of the piston hammer to change the valve means from directing air to one end of the chamber to directing air to the other end of the chamber. The first part of the sensing means described herein is the means for driving the valve means from the drive orientation (FIGS. 9 and 10) to the return orientation (FIGS. 11 and 12). Channel means supply air to the chamber. The channel means is part of a secondary air conduit means. In the exemplary embodiment, the channel means 101 (FIG. 10) is connected by a narrow bore 102 to the bore 54 of primary air conduit 51. Channel means 101 also has a secondary port 103 communicating with chamber 60 rearward of forward port 53. It should be noted that bore 102 is narrower than bore 54. Therefore, there will be a pressure drop over channel 101 and bore 102 so that air entering secondary port 103 is at a lower pressure than is air entering rear port 52 so that there is little pressure buildup at the forward end of the chamber and little cushioning of the piston moving in the drive direction. Moreover, air that does enter the chamber through secondary port 103 is exhausted from forward port 53 during the drive stroke.

The position of the piston hammer is sensed in the following manner. When piston hammer 70 reaches the position shown in FIG. 10, it blocks air from entering chamber 60 through secondary port 103. The valve sleeve 91 includes a radial flange 96 (FIG. 10) which extends into channel means 101 at cavity 104. When port 103 is covered and the pressure in channel 101 and cavity 104 increases, a force is exerted on flange 96 to the right (FIG. 10) to drive valve sleeve 91 to the return orientation shown in FIG. 12.

The dimensions of various faces of the valve sleeve which are exposed to air pressure are important. Valve sleeve 91 has a rear face 97 facing the rear of the chamber and a forward face 98 facing the forward end of the chamber. The rear face 97 has a larger area than the area of the forward face 98. In the FIG. 11 orientation, as the hammer is traveling in the return direction, air is exhausted out of exhaust port 67 until the piston hammer reaches the location of exhaust port 67. At that point, air in the rear end of the chamber will begin to become pressurized as the piston hammer 70 travels toward the rear end of the chamber. The increased pressure acts on rear face 97 of valve sleeve 91 to create a force urging the valve means back to the drive orientation (to the left in FIG. 11).

Along with the increase in pressure in the rear end of the chamber, the piston hammer 70 uncovers secondary port 103 so that air in channel means 101 can now flow into the forward part of the chamber decreasing the pressure in channel means 101 and cavity 104. Therefore, the pressure forces acting on flange 96 urging the valve sleeve 91 to the right are low. It should also be noted that air flowing into the forward end of the chamber through forward port 53 has pressurized the forward end of the chamber, but as piston hammer 70 passes to the right of exhaust port 67, pressure in the forward end of the chamber decreases. Moreover, because the forward face 98 of valve sleeve 90 has a relatively small area, any pressure in the forward end of the chamber acts over a small area. When the net force resulting from pressure on valve faces 97 and 98 and on the face of valve flange 96 are in a direction urging the valve to the drive orientation, the valve sleeve will so move.

It should also be recognized that the pressure in the rear end of the chamber is increasing rapidly so that the force, which is a product of the pressure in the area also increases rapidly.

Pilot pressure means supplies air to the rear of the chamber independent of the position of the valve to pressurize the rear of the chamber to cushion the return motion of the piston hammer and to supply a pressure on the rear face of the valve sleeve when the valve means is in the return orientation for driving the valve means to the drive orientation. As shown in FIGS. 9 and 11, the pilot pressure means comprises a pilot tube 57 which is connected to primary air conduit 51. The cross-sectional area of pilot tube 57 is substantially smaller than the combined area of the inlet bores 54 so that a much smaller volume of gas enters the rear of the chamber through pilot tube 57 than through the rear ports 52. After piston hammer 70 passes exhaust port 67 in its return to the rear of the chamber, the air in the rear of the chamber begins to be pressurized and the air entering through pilot tube 57 increases the pressure. The increased pressure cushions the return of the piston hammer so that it does not impact the rear wall of the chamber. Moreover, if rear face 71 of piston hammer 70 travels to the right (FIG. 12) of rear air ports 52, the air entering the port will be unable to pressurize rear face 71. The pressure which has built up in the rear of the chamber will initiate some driving movement, and the additional air provided by the pilot tube 57 will ensure that there is sufficient air pressure to initiate driving of the piston hammer. The additional air also assists in pressurizing the rear face 97 of valve sleeve 91 to assist in moving the valve to the left to the drive orientation.

The present invention also includes a method of impulse driving a member. Air is directed through a first air port 52 in a chamber 60 on one side of a piston hammer 70 to drive the piston hammer in a drive direction from a first to a second position. A smaller amount of air is directed through channel 56 into chamber 60 on the other side of piston hammer 70 adjacent the second position. A portion of a valve 90 is exposed to air pressure in channel 56, and the pressure in channel 56 is increased by blocking the channel outlet 103 to the chamber with the piston hammer when it approaches the second position. This moves the valve from a first position for opening the first air port 52 to a second position closing the first air port by the air pressure in the channel acting on a portion of valve 90 to stop air from entering the first air port 52. The movement of hammer 70 is reversed by opening a second air port 53 which opens into the chamber on the other side of piston hammer 70. The second air port is opened by the step of moving the valve to the second position to pressurize the other side of the piston hammer to return it to the first position. The chamber on the first side of piston hammer 70 is pressurized during return of the piston hammer. A first face 97 of the valve 90 is presented in the chamber on the first side of the piston hammer, and a second face 98 of the valve is presented on the other side of the piston hammber in the chamber. First face 97 has an area such that as piston hammer 70 approaches first air port 52, the product of the pressure in the chamber on the first side of the piston hammer multiplied by the area of first face 97 is greater than the product of the pressure in the chamber on the other side of the piston hammer multiplied by the area of second face 98.

4. Output of the Impulse Motor

As stated above, piston hammer 70 contacts impulse transmission means 80 whereby impulses can be transmitted to an output member such as chisel 10 or wire 20. As the mass of impulse transmission means 80 changes, the operation of the impacting changes. For example, assuming no resistance on the output member, if piston hammer 70 were of the same mass as impulse transmission means 80, when piston hammer 70 impacted on impulse transmission means 80, piston hammer 70 would stop and impulse transmission means 80 would move in the same direction as piston hammer 70 at the same velocity. If the piston hammer is heavier than the impulse transmission means, piston hammer 70 will continue at a slower velocity to the left while impulse transmission means 80 moves rapidly to the left, but if impulse transmission means 80 is substantially more massive than piston hammer 70, piston hammer 70 will rebound sharply while impulse transmission means moves but a small amount to the left. Of course if there is resistance on the output member, the effective mass of the impulse transmission means increases modifying the affect on the piston hammer.

Figure 6:
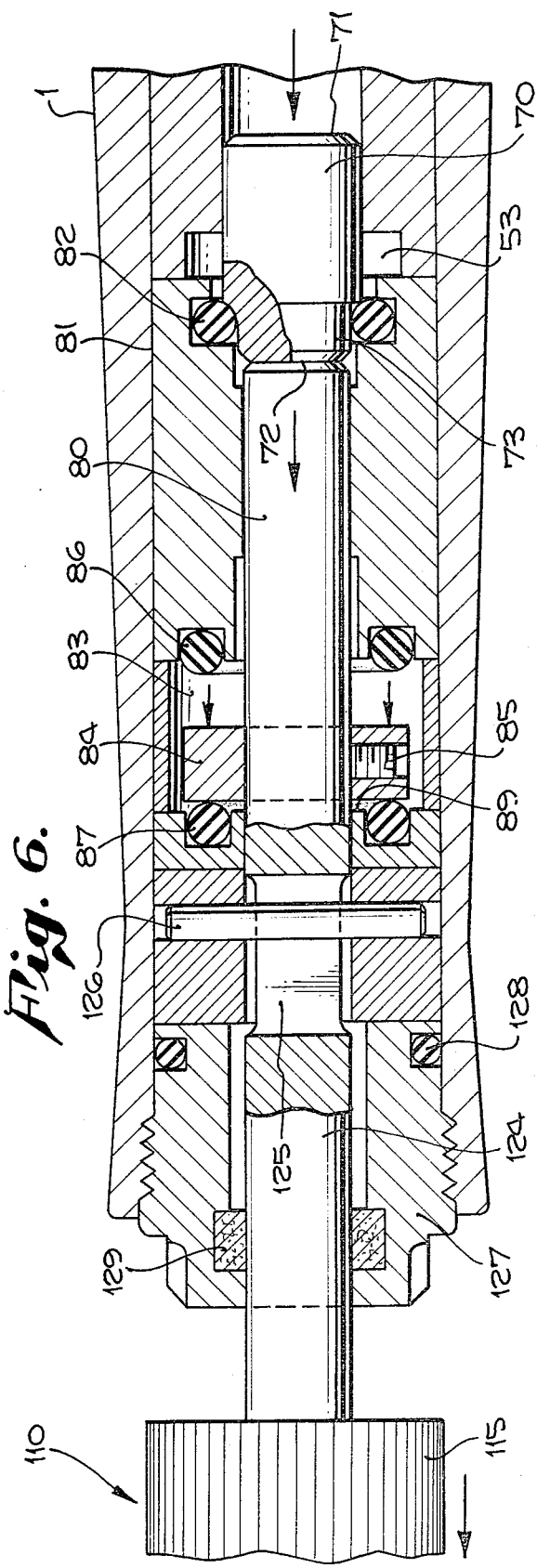
FIG. 6 shows the piston hammer impacting impulse transmission means for transmission to the output member, and also shows what is known as the stall condition of the impulse motor.

The tool of the present invention contemplates a stall feature. Normally, at the point of impact where piston hammer 70 contacts impulse transmission means 80, the reduced diameter portions 72 and 73 of the piston hammer is over air port 53 so that the air pressure can drive piston hammer in the return direction. However, depending on the weight of impulse transmission means 80 relative to piston hammer 70, after one or more strokes of the piston hammer which would move impulse transmission means 80 to the left, piston hammer 70 could move to the position shown in FIG. 6. There it can be seen that impulse transmission means 80 is mounted in impulse transmission housing 81. Resilient means which in the preferred embodiment comprises O-ring 82 grip and cushion smaller diameter portion 73 of piston hammer 70 when the piston hammer extends into pulse transmission housing 81. In the FIG. 6 position, it should be noted that although air is being directed from the primary air conduit to forward air port 53, the piston hammer 70 is blocking entrance of the air into the chamber so that the motor stalls. In order to restore the motor to operation, the tool can be pushed against the workpiece which would drive impulse transmission means to the right (FIG. 6) and move the narrow diameter portion 73 over air port 53 to initiate return of the piston hammer.

The tool using the stall feature has an advantage in that no impulses are transmitted unless a resistance occurs on the output member because only a resistance will restore impulse transmission means 80 to the right so that it assumes the position shown for example in FIG. 7. Therefore, with the stall feature, the operator can keep the handle 43 depressed with the motor "on", and the impulse motor will only be driven when the output member is pushed against the workpiece.

Some users may find it difficult to become accustomed to the stall feature because it requires that resistance occur on the output member before the impulse motor operates. Therefore, means are provided to override the stall feature. Turning to FIGS. 2 and 15 in the preferred exemplary embodiment, impulse transmission housing 81 has a cavity or compartment 83, and annular nub 84 which is attached to impulse transmission means 80 and fixed thereon by means of set screw 85 moves in the compartment 83. Resilient means in the form of O-rings 86 and 87 are provided at the walls of compartment 83 to cushion the impact of nub 84 with the walls of compartment 83.

Separate resilient means are mounted between the nub and the wall 89 of the compartment means near the output member for absorbing movement of the impulse transmission means to restore the impulse transmission means to the position where it will be impacted by the impulse motor. In the preferred embodiment especially as shown in FIGS. 2 and 15, the additional resilient means comprises a quadring 88 of elastic material which in its relaxed condition is approximately the width between the nub 84 and wall 89.

When impulses are transmitted to the impulse transmission means 80 causing movement thereof, resilient member 88 will be compressed and will restore impulse transmission means 80 to the position shown in FIGS. 2 and 15 so that impulse transmission means 80 can receive impacts from piston hammer 70. With the stall override feature, the impulse motor operates independently of the resistance to the output member.

Resilient member 88 also allows the operator to adjust the amount of power transmitted to the workpiece by the pressure he bears against it. If the output member is lightly held against the workpiece, part of the impulse forces are absorbed by the resilient member 88 and the remainder is transmitted through the output member, either chisel 10 or wire 20. On the other hand, as the force urging the tool against the workpiece is increased, more of the impulse forces are transmitted through the output member.

5. The Chisel and Means for Holding the Chisel

The remaining discussion essentially deals with the output member whether it be the chisel shown in FIGS. 1 through 6 or the wire driver as shown in FIGS. 15, 16 and 17. The surgical tool of FIG. 1 has an impulse motor 50, a chisel 10 and impulse transmission means for transmitting impulses from the impulse motor to the chisel. Securing means secures the chisel to the impulse transmission means. The improvement comprises the provision of having detent means on the chisel. In the exemplary embodiment, especially FIGS. 1 through 5, chisel 10 has a square shank portion 11 with detents 12 along the edges of the shank near the rear thereof. Chisel 10 narrows from shank 11 to cutting edge 13 where it can be used to chip away bone or other hard material.

The improvement also comprises having securing means shown generally at 110 for securing chisel 10 to impulse transmission means 80. The securing means comprises supporting means attached to the impulse transmission means for supporting the chisel. In the exemplary embodiment, the supporting means is integral with impulse transmission means 80. Support means 111 has a wide diameter portion 112 and a narrow diameter portion 113 extending forward of the wide diameter portion 112. Wide diameter portion 112 has threads 114. Housing member 115 fits over the chisel securing means and is threadably connected to threads 114 of wider diameter portion 112. As shown primarily in FIG. 3, securing means 110 has a generally circular cross section with square bore 116 for supporting the square shank 11 of the chisel therein. Bore 116 terminates in a rear wall 117.

Slot means in the supporting means is located above the detent means. The detent means 12 is positioned on the chisel such that when chisel rear wall 14 is against bore wall 117, detent 12 is situated below slot 118 through narrow diameter portion 113 of chisel securing means 110.

Contacting means in the slot means move into and out of the detent means. In the exemplary embodiment, the contacting means comprises a spherical member or a ball 119 in slot 118 movable into and out of the detent means 12. Slot 118 is slightly tapered (FIG. 3) or it may be counterbored to limit travel of the ball and prevent the ball from falling entirely into bore 116. Locking means in housing 115 and means for mounting the locking means for movement in the housing to exert force on the contact means to the detent means to hold the chisel in the supporting means are also provided. Locking means 120 moves axially in the housing relative to the supporting means. In the exemplary embodiment in FIG. 2, locking means 120 has moved to the right and is urging ball 119 against detent 12. On the other hand, when housing 115 is unscrewed (FIG. 5), locking means 120 moves to the left relative to the supporting means 110 so that ball 119 can move out of the detent 12 to the phantom line position.

Figure 5:
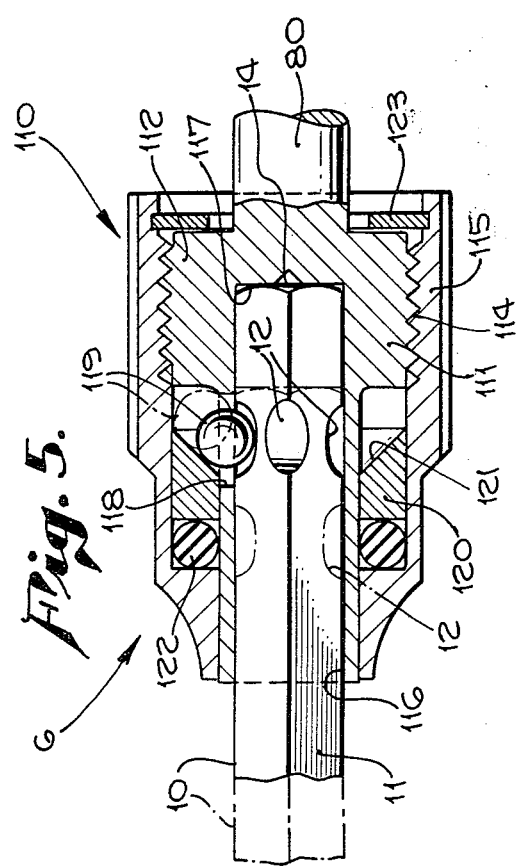
FIG. 5 is a sectional view of the holding means similar to FIG. 4 but showing the holding means receiving and holding the chisel.

Locking means 120 has an inclined face 121 inclined to the axis of the chisel at an angle of approximately 45° to the axis of the chisel. The inclined face contacts the ball and exerts force on the ball directing force axially and radially to the detent means. As shown in FIGS. 2, 4 and 5, the detent has a dimension axially on the chisel which is greater than the diameter of the ball 119. This feature is important because it prevents the securing means from being jammed in the locked condition. As shown in FIGS. 2 and 4, in operation the ball is against the rear portion of detent 12. When impulses are transmitted by the impulse transmission means 80 to the chisel, the chisel will be urged to the left and the rear part of the detent will be forced against ball 119. The force urges the ball upward and to the left. However, the locking means 120 prevents the ball from moving and secures it against the rear portion of detent 12. Of course the force from the ball 119 acting on locking means 120 is transmitted to housing 115, but shock absorbing means in the form of O-ring 122 contacts locking means and absorbs energy from the impulse transmission means to limit the amount of force between the housing 115, the locking means 120, ball 119 and chisel 10.

If inclined face 121 is at a very much smaller angle to the axis of the chisel, ball 119 will have a tendency to submarine under locking means 120 so that the force will be directed downward against the chisel rather than rearward to the rear face of detent 12. Increasing the force upward on locking means 120 urges it against the housing 115, and as the forces become larger, it may be difficult to rotate housing 115 with respect to locking means 120 causing jamming of the mechanism. Without the shock absorbing means in the form of O-ring 122, even with the inclined face, the large forces developed during impulsing would still tend to cause the locking means to ride over the ball to jam the mechanism. Although the securing means does provide downward force to urge the shank 111 against the bore 116, it must also hold the chisel tightly so that the rear wall 14 of the chisel contacts rear wall 117 of bore 116.

The chisel securing means of the present invention is operated in the following manner. The securing means is oriented to the FIG. 5 configuration by moving housing 115 to the right relative to securing means 110, until housing rear wall 123 contacts the wider diameter portion 112 of the support means 111. The chisel is inserted into bore 116. Ball 119 can move upward to the phantom position in order to accommodate shank 11 and can drop into the slot 118 and into detent 12.

After the ball 119 is in detent 12, housing means 115 is rotated until it reaches the FIG. 2 configuration where inclined face 121 of locking means 120 is urging ball 119 against the rear of detent 12. In this configuration, the tool is ready to use.

When the impulse motor is activated, impulses are transmitted by impulse transmission means 80 to integral support means 111. Impulse transmission means 80 used with the chisel in the preferred embodiment is a solid shaft 124 which has a slot at 125. Pin 126 is secured in the housing and is mounted in slot 125. The pin 126 prevents rotation of impulse transmission means relative to the housing. Cap 127 is threaded into housing 1 and O-ring 128 seals the cap in the housing. Seal 129 prevents contaminates from leaking into impulse transmission means housing 81. The movement of shaft 124 and slot 125 relative to pin 126 is seen by comparing FIGS. 2 and 6.

Force from impulse transmission means 80 is transmitted to support means 111 which urges the chisel forward. The forward impulse of the chisel is transmitted to ball 119 and then to locking means 120 where it can be absorbed by O-ring 122. Most of the force is transmitted to the cutting edge or tip of the chisel 13 to chip bone or other hard material 3. By absorbing the excess forces in O-ring 122 (FIG. 4), jamming of the securing means is prevented. If the chisel is to be removed or replaced, the housing is rotated in the opposite direction sliding locking means to the left or FIG. 5 orientation. Thereafter, pulling on the chisel will urge the ball 119 upward against housing 115 so that the chisel can be removed.

6. Wire Driver

The surgical tool of the present invention may also be used to drive wire. In that instance, the chisel holder would be replaced by a wire holder. It is contemplated that both the wire holder and the chisel holder would not be changeable accessories to an impulse motor. A complete wire driver and a complete impulse chisel would be provided. The wire driver uses an output transmission means modified from that used with the chisel. Sealing problems are also anticipated with interchangeable holders. Therefore, even though the present invention could be designated to accept both holders, the exemplary embodiments are entire tools with either a wire holder or a chisel holder.

As stated above, wire can be inserted into bone or other hard material, but the previous method of inserting it is to rotate the wire to remove material. However, this method creates excess heat which can damage the surrounding tissue. Therefore, in the present invention, the surgical tool which has holding means for holding the wire in the tool and for locating the end of the wire which is to be driven through the hard material has been improved by including impulse driving means for providing impulses to the holding means to drive the wire in a series of small impulses through the hard material. The holding means of the present invention supports wire 20 partially within the tool and extending out of one end. (FIGS. 15–17) The holding means includes guide means for supporting wire 20. In the exemplary embodiment, guide means comprises an elongated tube 142 which is mounted in housing 143 and which supports wire 20. Supplemental guide 144 is mounted within tube 142 and has an inside diameter approximately equal to the outside diameter of the wire 20. It is contemplated that for each different diameter wire, a separate supplemental guide would be provided. The supplemental guide prevents buckling of the wire while it is driven.

Gripping means or clamping means extends through the guide means for gripping the wire and collet means around the guide means adjacent to the gripping means. In the exemplary embodiment, especially FIGS. 15 and 17, the gripping or clamping means comprises one or more wafers 145 (three wafers are provided in the exemplary embodiment spaced 120° apart) extending through apertures 146 through the elongated tube 142 which comprises the guide means. Each wafer 145 has a flat wire gripping surface 147 facing radially inward to grip the wire along the length thereof. Large forces are developed in the impulsing of the tool and the flat wire gripping surface spreads the force over a larger portion of wire 20. If smaller gripping or clamping means are employed, there may be a tendency to localize the force over a small area of wire which could cut through the wire. The width w (FIG. 16) of each wafer must be narrow enough so that the wafers can be inserted a sufficient distance to grip small diameter wires. Wider wafers will intersect each other before being able to grip narrow wires.

Each wafer also has an inclined surface 148 which intersects the wire gripping surface on the end of the wafer near the end of the wire driven into the bone (i.e. the left end of wafer 145 in FIGS. 17 and 19) for spreading the wafers when wire is inserted into the guide means and contacts the wafers. As will become apparent, when the rear end 21 of the wire is inserted through the guide means, it will contact inclined surface 148 of each wafer 145 to spread them apart.

Collet means 149 has a tapered end having a larger inside diameter at 150 at the forward end of the tool where the wire is driven (left end of FIGS. 15 and 17) tapering to a smaller diameter at 151 away from the end of the tool. Apertures 146 through guide means 142 are under the tapered portion of the collet.

Collet 149 is movable between two positions. The second position of the collet has the greater inside diameter 150 over the aperture to allow the wafers to move radially outward away from the inside of the guide means and out of gripping contact with the wire to permit movement of the wire in the guide means. The second position is achieved in the following manner. Housing 143 is urged to the left (FIG. 17) which urges guide means 142 in the same direction. Apertures 146 therefore move along the tapered surface of collet 149 toward the larger diameter portion 150. This lessens the force from the collet 149 through the wafers 145 to the wire 20 and allows the wire to be moved in either direction through guide means 142. However, when the housing is released, spring bias from spring 152 urges collet 149 and member 153 apart. As member 153 is connected to housing 143, and housing 143 is connected to guide means 142, the spring moves collet 149 to a first position relative to the guide means. At the first position (FIG. 15), the smaller inside diameter portion 151 is over the apertures to force the wafers 145 inward into the guide means to grip wire 20 and prevent its movement in the guide means.

Three wafers are used in the exemplary embodiment because more than two are needed in order to grip the wire and prevent both horizontal and vertical movement of the wire, and four wafers would have a tendency to interfere with each other and not permit the use of narrow wires.

The wire is driven in the following manner. Piston hammer 70 impacts on to impulse transmission means 80. The impulse transmission means used with the wire driver comprises a hollow shaft 155 having cap 156 at the impacting end to protect the end of shaft 155 from impacts from piston hammer 70. Shaft 155 must be hollow in order to accommodate the wire 20 which is partially stored within the shaft 155. In the exemplary embodiment, collet 149 is formed integrally with shaft 155. Forces from the impulse motor are transmitted to shaft 155 to collet means 149. The impulses, therefore, drive collet 149 to the left (FIG. 15) urging narrower diameter portion 151 over aperture 146 to urge wafer 145 against wire 20. The collet therefore receives impulses from the impulse motor and transmits the impulses through wafers 145 to wire 20.

In use, a short length of wire 20 extends out of supplemental guide 144 and is placed where needed along bone 4. The impulse motor is activated and a short length of wire is driven by impulses into the bone. If the tool has a stall feature, resistance will have to be supplied in order to prevent stalling of the motor. If an override feature is included in the tool such as resilient member 88 in the form of a donut, impulsing will occur as long as handle 43 is depressed. After a short length of wire is inserted into the bone, the tool is stopped and wire must be pulled from the tool. This may be accomplished two ways. Either housing 143 can be moved to the left (FIG. 19) which moves the guide means 142 to wider diameter portion 150 to release the wafer from the wire or the end of wire 20 extending out of the tool can be pulled which tends to pull wafers 145 to the wider diameter portion 150 of collet 149. Therefore, it can be seen that the present arrangement for holding the wire in the tool only prevents wire from being moved into the tool (to the right in FIGS. 15 and 17) and will not prevent wire from being pulled from the tool. This is a desirable result because each time a short length of wire is inserted into the bone, another small length must be removed from the tool. The present driving system and holding arrangement is considered to be most advantageous because it is the actual impulses transmitted from the motor through shaft 155 to collet 149 which force wafers 145 against the wire. No other mechanical connection is necessary. For example, if the collet depends on spring bias to remain tight during each impulse, the high frequency of the tool can render the spring useless; it will only vibrate and not provide any force. A different mechanical system depending on rotation of members relative to the collet can be exceedingly slow. If a member must be rotated while the wire withdrawn and then rotated again to lock the chuck, the tool can be difficult and time consuming in use. The present invention is much simpler in use because either a force can be exerted on the housing 143 which moves the guide means 142 relative to the collet, or by pulling the wire out of the tool, wafers 145 which are coupled to guide means 142 moves the guide means and the wafer under the wider diameter portion 150 at the collet to allow wire to be withdrawn from the tool.

The gripping means in the form of wafers 145 also has a top face 151 which may be inclined at the same angle as the taper of the collet to provide more positive gripping of the wafer 145 by collet 149. To ensure even better gripping, the top face 151 of wafer 145 could be slightly curved to conform to the conical inside of the collet.

Although it can be seen that there are differences between the chisel holder and the wire holder, there are similarities. Both have guide means 113, 142 for supporting the impacting member 10, 20, gripping means 119, 145 extending through the guide means for gripping the impacting member and collet means 115 and 120 in the case of the chisel and 149 in the case of the wire which are around the guide means adjacent to the gripping means. Both collets are movable between a first position urging the gripping means into the guide means and a second position releasing the gripping means to release the impacting member. However, in the chisel, impacting is done at one end of the chisel which urges the gripping means through detent 12 against locking means 120. In order to prevent buckling of the wire, the wire must be driven as near to the work as possible and therefore cannot be driven at its end. Therefore, the drive for the wire comes from the collet. In the chisel, the collet is more passive, serving to grip the chisel rather than to drive it.

The present invention also includes a method for driving wire and includes supporting the wire in a guide and then contacting the wire by pushing gripping means through apertures in the guide. The gripping means are surrounded with a collet having an inclined face against the gripping means. The collet is then impacted with an impulse motor to be driven against the gripping means along the inclined face of the collet to urge the gripping means against the wire, gripping the wire and moving it in impulses to drive it into the bone or other hard material.

7. Conclusion

Thus, a surgical tool using an impulse motor to drive a chisel or a wire into bone or other hard material has been shown. The novel impulse motor used to drive the tool has been explained in detail concentrating especially on the novel features disclosed therein. The method of impulse driving has been explained also. Thereafter, the holder for the tools was discussed. First discussed was the chisel holder which secures chisel 10 into chisel securing means 110. Next discussed was the wire driver holding wire 20 into its holding means 140. The method of driving wire into bone or other hard material was also discussed in detail with particular emphasis on the novel features thereof. The objects of the invention have been met, and other objects became apparent from the description of the surgical tool.

It will be understood that various modifications and changes may be made in the configuration described above which may come within the spirit of this invention and all such changes and modifications coming within the scope of the appended claims are embraced thereby.

I claim:

1. In a surgical tool including an impulse motor, an output member for removing or breaking through tissue and impulse transmission means for transmitting impulses from the impulse motor to the output member, a chamber and a piston hammer movable in the chamber from an initial position at the rear end of the chamber to an impacting position impacting the impulse transmission means at the forward end of the chamber, air supply means for supplying air to the ends of the chamber, valve means in the chamber for directing air to one or the other end of the chamber, and sensing means on the valve means for sensing the position of the piston hammer to change the valve means from directing air to one end of the chamber to directing air to the other end of the chamber, the improvement comprising:

the output means comprises a holding means for holding a chisel, the holding means comprising supporting means attached to the impulse transmission means for supporting the chisel, a ball extending through the supporting means for gripping the chisel and collet means around the supporting means adjacent to the ball, the supporting means and the collet means being movable relative to each other between a first position wherein the collet means urges the ball into the supporting means to grip the chisel and a second position releasing the ball to release the chisel, detent means on the chisel, slot means in the supporting means located above the detent means, the ball being located in the slot means for movement into and out of the detent means, locking means mounted in the collet means for axial movement with the collet means to exert force on the ball so that the ball moves into the detent means to hold the chisel in the supporting means, and the detent means comprising a curved surface which has a dimension axially on the chisel which is greater than the diameter of the ball, the locking means comprises inclined face means inclined to the axis of the chisel for exerting force on the ball and directing the force on the ball axially and radially to the portion of the curved surface of the detent means nearer the rear of the chisel, and shock-absorbing means in the collet means and contacting the locking means for absorbing energy from the impulse transmission means to limit the amount of force between the collet means, the locking means, the ball and the chisel.

2. In a surgical tool including an impulse motor, an output member for removing or breaking through tissue and impulse transmission means for transmitting impulses from the impulse motor to the output member, a chamber and a piston hammer movable in the chamber from an initial position at the rear end of the chamber to an impacting position impacting the impulse transmission means at the forward end of the chamber, air supply means for supplying air to the ends of the chamber, valve means in the chamber for directing air to one or the other end of the chamber, and sensing means on the valve means for sensing the position of the piston hammer to change the valve means from directing air to one end of the chamber to directing air to the other end of the chamber, the improvement comprising:

the output means comprises a holding means for holding an impacting member, the impacting member being a wire, the holding means comprising guide means for supporting the impacting member, the impulse transmission means having a central bore aligned with the guide means for receiving a portion of the wire, gripping means extending through the guide means for gripping the impacting member and collet means around the guide means adjacent to the gripping means, the guide means and the collet means being movable relative to each other between a first position wherein the collet means urges the gripping means into the guide means to grip the impacting member and a second position releasing the gripping means to release the impacting member, the guide means is an elongated tube having at least one aperture therethrough, the clamping means comprising a wafer extending through each aperture, the collet means having a tapered end having a larger inside diameter at the end of the tool where the wire is driven tapering to a smaller diameter away from said end of the tool, the aperture being under said tapered portion, the second position of the collet having the greater inside diameter over the aperture to allow the wafers to move radially outward away from the inside of the guide means and out of gripping contact with the wire to permit movement of the wire in the guide means, and the first position of the collet having the smaller inside diameter over the aperture to force the wafers radially inward into the guide means to grip the wire and prevent its movement in the guide means, means connecting the collet means to the impulse transmission means to transmit impulses to the collet means, means interconnecting the collet means to the gripping means and means connecting the gripping means with the wire for transmitting impulses from the collet means through the gripping means to the wire.

3. In a surgical tool including an impulse motor, an output member for removing or breaking through tissue, the output member comprising a wire, and impulse transmission means for transmitting impulses from the impulse motor to the output member, a chamber and a piston hammer movable in the chamber from an initial position at the rear end of the chamber to an impacting position impacting the impulse transmission means at the forward end of the chamber, air supply means for supplying air to the ends of the chamber, valve means in the chamber for directing air to one or the other end of the chamber, and sensing means on the valve means for sensing the position of the piston hammer to change the valve means from directing air to one end of the chamber to directing air to the other end of the chamber, the improvement comprising:

the output means comprises a wire holding means for holding the wire proximate to tissue for driving the wire into the tissue, the holding means comprising chuck means for preventing the wire from being pushed into the tool during the impulses but allows withdrawal of wire from the tool if force is applied on the wire to remove it from the tool, the holding means comprising guide means for supporting the wire within the holding means, clamping means extending into the guide means for gripping the wire, collet means around the guide means for movement from a first position relative to the guide means urging said clamping means into engagement with the wire and a second position relative to the guide means not urging said clamping means into engagement with the wire, the impulse transmission means having a central longitudinal bore aligned with the guide means for receiving a portion of the wire.

4. The improvement of claim 6 wherein the shock-absorbing means is directly forward of and adjacent to the locking means and rearward of and adjacent to a portion of the collet to absorb forces along the axis of the chisel.

* * * * *

UNITED STATES PATENT AND TRADEMARK OFFICE
CERTIFICATE OF CORRECTION

PATENT NO. : 4,298,074
DATED : Nov. 3, 1981
INVENTOR(S) : Terry M. Mattchen

It is certified that error appears in the above-identified patent and that said Letters Patent are hereby corrected as shown below:

Column 18, line 13 (line 1 of claim 4), change "6" to --1--.

Signed and Sealed this

Sixteenth Day of March 1982

[SEAL]

*Attest:*

*Attesting Officer*

GERALD J. MOSSINGHOFF
*Commissioner of Patents and Trademarks*